(12) United States Patent
Voelker

(10) Patent No.: US 8,912,237 B2
(45) Date of Patent: Dec. 16, 2014

(54) STABILIZED CAROTENOID COMPOSITIONS

(71) Applicant: Karl Manfred Voelker, Freiburg (DE)

(72) Inventor: Karl Manfred Voelker, Freiburg (DE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/941,428

(22) Filed: Jul. 12, 2013

(65) Prior Publication Data
US 2014/0018442 A1 Jan. 16, 2014

Related U.S. Application Data

(63) Continuation of application No. 11/995,619, filed as application No. PCT/EP2006/006580 on Jul. 6, 2006, now abandoned.

(30) Foreign Application Priority Data

Jul. 20, 2005 (EP) .................... 05015734

(51) Int. Cl.
*A01N 47/00* (2006.01)
*A23L 1/09* (2006.01)
*A23L 1/303* (2006.01)
*A23L 1/0522* (2006.01)
*A23K 1/16* (2006.01)
*A61Q 19/00* (2006.01)
*C09B 61/00* (2006.01)
*A61K 8/31* (2006.01)
*A61K 31/015* (2006.01)
*A61K 47/06* (2006.01)
*C09B 67/46* (2006.01)
*A23L 1/053* (2006.01)
*A61K 8/73* (2006.01)
*A23L 1/275* (2006.01)

(52) U.S. Cl.
CPC .............. *A23L 1/2753* (2013.01); *A23L 1/095* (2013.01); *A23L 1/303* (2013.01); *A23L 1/0522* (2013.01); *A23K 1/1603* (2013.01); *A61K 2800/522* (2013.01); *A61Q 19/00* (2013.01); *C09B 61/00* (2013.01); *A61K 8/31* (2013.01); *A61K 31/015* (2013.01); *A23V 2002/00* (2013.01); *A61K 47/06* (2013.01); *A23K 1/1606* (2013.01); *C09B 67/0089* (2013.01); *A23L 1/053* (2013.01); *A61K 2800/43* (2013.01); *A61K 8/732* (2013.01)
USPC .......................................... 514/778; 426/540

(58) Field of Classification Search
None
See application file for complete search history.

(56) References Cited

U.S. PATENT DOCUMENTS

| | | | |
|---|---|---|---|
| 3,998,753 | A | 12/1976 | Antoshkiw et al. |
| 4,713,251 | A | 12/1987 | Seighman |
| 6,406,735 | B2 | 6/2002 | Stein et al. |
| 2003/0148099 | A1 | 8/2003 | Defreitas et al. |
| 2004/0235787 | A1 | 11/2004 | Beck et al. |

FOREIGN PATENT DOCUMENTS

| | | |
|---|---|---|
| DE | 10 35 319 | 7/1958 |
| JP | 57 3861 | 1/1982 |
| WO | 91/06292 | 5/1991 |
| WO | 03/022071 | 3/2003 |
| WO | 2006/032399 | 3/2006 |

OTHER PUBLICATIONS

International Search Report mailed Sep. 6, 2006.
Written Opinion of the International Searching Authority mailed Sep. 6, 2006.
International Preliminary Report on Patentability dated Jun. 25, 2007.

*Primary Examiner* — Suzanne Ziska
(74) *Attorney, Agent, or Firm* — Nixon & Vanderhye P.C.

(57) ABSTRACT

The present invention relates to novel compositions containing finely dispersed carotenoids. The novel compositions of this invention can be used as colorants or additives for food, beverages, animal feeds, cosmetics or drugs. The colorant composition may be a liquid or a solid composition. The solid composition comprises at least one carotenoid which is dispersed in a matrix, wherein the matrix contains at least one carbohydrate and/or one modified carbohydrate and optionally, a protein, a modified protein or mixtures thereof, wherein the at least one carbohydrate and/or one modified carbohydrate is starch or modified starch, wherein the amount of starch or modified starch is from about 10 wt-% to 60 wt-% of based on the total weight of the matrix, and wherein the concentration of the at least one carotenoid is at least 2% based on the total weight of the composition. Preferably β-carotene is used as a solid water-dispersible colorant composition.

6 Claims, 1 Drawing Sheet

STABILIZED CAROTENOID COMPOSITIONS

CROSS-REFERENCE TO RELATED APPLICATIONS

This application is a continuation of commonly owned U.S. application Ser. No. 11/995,619, filed Apr. 15, 2008 (now abandoned), which is the national phase application of International Application PCT/EP2006/006580, filed Jul. 6, 2006, which designated the US and claims benefit of EP Patent Application No. 05015734.6, filed Jul. 20, 2005, the entire contents of each of which are hereby incorporated by reference.

FIELD

The present invention relates to novel compositions containing finely dispersed carotenoids. The novel compositions of this invention can be used as colorants or additives for food, beverages, animal feeds, cosmetics or drugs.

BACKGROUND AND SUMMARY

The colorant composition may be a liquid or a solid composition. Preferably β-carotene is used as a solid water-dispersible colorant composition. The liquid colorant compositions may be a stable aqueous dispersion of β-carotene. In order to achieve an intermediate color hue, these compositions may optionally contain another coloring compound, e.g. another carotenoid such as β-zeacarotene, canthaxanthin, 8'-apo-β-carotenal, 8'-apo-β-carotenoic acid ethyl ester, lycopene, astaxanthin, lutein and zeaxanthin.

Solid water-dispersible colorant compositions are compositions wherein β-carotene is finely dispersed in a matrix or carrier. The matrix or carrier can be any matrix or carrier conventionally used for formulation of carotenoids. For example, the carrier can be a carbohydrate, a modified carbohydrate, a protein, a modified protein, or a mixture thereof.

The preparation of such colorant compositions for use in the present invention can be carried out in a manner known per se for the preparation of carotenoid and fat soluble vitamin compositions for use in food and beverages, e.g. as disclosed in European patent publications nos. 0 347 751, 0 966 889, 1066 761, 1 106 174 and International patent application WO 98/15195, the contents of which are incorporated herein by reference.

A preferred procedure to prepare a colorant composition in accordance with the present invention is to prepare a solution of β-carotene and an oil-soluble antioxidant in a triglyceride and, optionally, an organic solvent, e.g., a chlorinated hydrocarbon and to emulsify the oily solution in an aqueous solution prepared from a protective hydrocolloid carrier such as a protein, a polysaccharide or a modified polysaccharide or mixtures thereof, a carbohydrate and, optionally, a water-soluble antioxidant, removing the organic solvent if required, e.g. by evaporation.

The so-obtained oil-in-water dispersion can be converted into a solid composition, e.g. a dry powder using conventional technologies such as spray-drying, spray drying in combination with fluidized-bed granulation (the latter technique commonly known as fluidized spray drying or FSD), or by a powder-catch technique where sprayed emulsion droplets are caught in a bed of an absorbant such as starch and subsequently dried.

Well known solid colorant compositions containing β-carotene in amount of approximately 1 wt-% have an orange shade. Such compositions are dispersible in water and generate a yellow shade in food, beverages, animal feeds, cosmetics or drugs. For economical reasons it would be advantageous to increase the carotenoid concentration in this type of water-dispersible compositions. It is therefore an object of the invention to suggest a new water-dispersible colorant composition with a comparable color shade but with an increased carotenoid concentration.

It is generally known that colorant compositions for use in beverages should have high color intensity as well as a relatively high turbidity. It has now been found, surprisingly, that variation of the content of starch or modified starch, if this compound is used as part of the carrier or matrix, has an effect on color intensity and turbidity, on the red color value and on particle size. It has been further found that by using 10% to 60% of starch or modified starch based on the total weight of the carrier or matrix, the concentration of β carotene can be increased to at least 2%, preferably to 2% to 10%, more preferably to 2% to 5% based on the total weight of the composition, wherein the final composition has still sufficient properties in relation to color intensity and turbidity.

The stated object of the invention is therefore achieved by a colorant composition as described and claimed herein.

BRIEF DESCRIPTION OF THE DRAWINGS

The accompanying FIGURES are graphs showing the dependency of various parameters versus the content of Capsul (Starch derivatives) based on a mixture of Capsul and Arabic gum in a composition containing about 3 wt-% of β-carotene, wherein.

DETAILED DESCRIPTION

Figure 1:
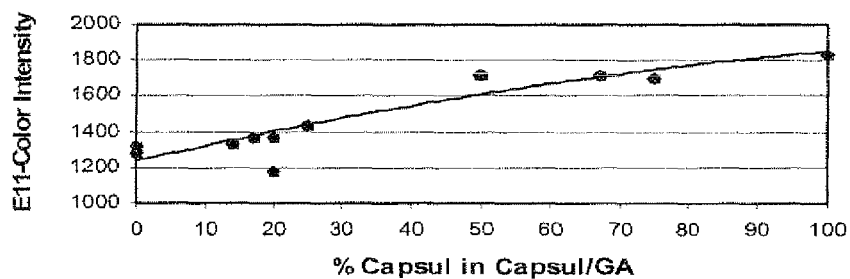
FIG. 1 shows the dependency of the color intensity E11 corresponding to 494 nm.

The term "carotenoid" as used herein comprises a carotene or structurally related polyene compound which can be used as a colorant for food, beverages, animal feeds, cosmetics or drugs. Examples of such carotenoids are α- or β-carotene, 8'-apo-β-carotenal, 8'-apo-β-carotenoic acid esters such as the ethyl ester, canthaxanthin, astaxanthin, lycopene, lutein, zeaxanthin or crocetin, or mixtures thereof. As already mentioned, the preferred carotenoid is β-carotene.

The carrier or matrix which is present in the composition of the present invention contains in addition to food starch or modified food starch, e.g. sodium octenyl succinyl starch, octenylbutanedioate amylodextrin (Capsul™), a polysaccharide gum such as gum Arabic, or a maltodextrin, or a protein such as gelatin, e.g. fish gelatin or swine or bovine gelatin, or a plant protein, or a milk protein or a ligninsulfonate or mixtures thereof.

Suitably, the novel compositions of this invention further contain adjuvants and/or excipients such as one or more of a mono- di-, oligo- or polysaccharide, a triglyceride, a water-soluble antioxidant, and/or one or more of a fat-soluble antioxidant. Solid compositions may also contain an anti-caking agent, such as silicic acid, and water.

Examples of mono- and disaccharides which may be present in the compositions of the present invention are sucrose, invert sugar, glucose, fructose, lactose, maltose and sugar alcohols.

Examples of triglycerides which may be present in the compositions of the present invention are middle chain triglycerides, vegetable oils, such as corn oil, sunflower oil, soybean oil, safflower oil, rape seed oil, arachis oil, palm oil, palm kernel oil, cotton seed oil or cocos oil.

The water-soluble antioxidant may be ascorbic acid and salts thereof, e.g., sodium ascorbate, and the like. The fat-soluble antioxidant may be a tocopherol, e.g., dl-α-tocopherol (i.e., synthetic tocopherol), d-α-tocopherol (i.e., natural tocopherol), β- and γ-tocopherol and mixtures thereof; butyl hydroxy toluene, butyl hydroxy anisol, propyl gallate, t-butyl hydroxy quinoline or ascorbic acid esters of fatty acids such as ascorbyl palmitate or stearate. Depending on the pH of the aqueous matrix solution the latter two compounds may alternatively be added to the water phase.

Typically, a powder composition according to the present invention comprises
- about 10 to about 60 wt.-%, preferably about 20 to about 30 wt.-% of sugar polymer, for example Maltodextrin;
- about 5 to about 50 wt.-%, preferably about 10 to about 40 wt.-% of gum Arabic;
- about 0.2 to about 10 wt.-% preferably about 1.5 to about 10 wt.-% of a carotenoid;
- 5 to about 15 wt.-% preferably about 5 to about 10 wt.-% of a mono- or disaccharide;
- 10 to about 50 wt.-% preferably about 15 to about 50 wt.-% of starch and modified starch;
- about 5 to about 50 wt.-% preferably about 10 to about 20 wt.-% of a triglyceride;
- 0 to about 5% preferably about 0.1 to about 2 wt.-% of a water-soluble anti-oxidant;
- 0 to about 5% preferably about 0.01 to about 1 wt.-% of a fat-soluble anti-oxidant;
- 0 to about 2 wt.-% preferably about 0.1 to about 1 wt.-% of silicic acid; and
- 0 to about 10 wt.-% preferably about 1 to about 5 wt.-% of water; the percentages of all ingredients totaling 100.

The novel compositions of this invention can find use as colorants for food, beverages, animal feeds, cosmetics or drugs. By the present invention there are preferably provided compositions comprising β-carotene as a coloring agent. Beverages wherein β-carotene can be used as a colorant can be carbonated beverages e.g., flavored seltzer waters, soft drinks or mineral drinks, as well as non-carbonated beverages e.g. flavored waters, fruit juices, fruit punches and concentrated forms of these beverages. They may be based on natural fruit or vegetable juices or on artificial flavors. Also included are alcoholic beverages and instant beverage powders. Besides, sugar containing beverages diet beverages with non-caloric and artificial sweeteners are also included.

Further, dairy products, obtained from natural sources or synthetic, are within the scope of the food products wherein the composition according to the invention can be used as a colorant. Typical examples of such products are milk drinks, ice cream, cheese, yoghurt and the like. Milk replacing products such as soy milk drinks and tofu products are also comprised within this range of application.

The novel compositions of this invention can also find use as colorants for confectionery products, candies, gums, desserts, e.g. ice cream, jellies, puddings, instant pudding powders and the like as well as for cereals, snacks, cookies, pasta, soups and sauces, mayonnaise, salad dressings and the like.

For coloration of a food or a pharmaceutical product a composition of this invention can be used according to methods per se known for application of water or oil dispersible solid or liquid carotenoid forms.

In general the β-carotene colorant composition may be added either as an aqueous stock solution, a dry powder mix or a pre-blend with other suitable food ingredients according to the specific application. Mixing can be done e.g. using a dry powder blender, a low shear mixer, a high pressure homogenizer or a high shear mixer depending on the formulation of the final application. Mixing procedure and amount of oily or aqueous ingredients may impact the color of the final application. As will be readily apparent such technicalities are within the skill of the expert.

The following Examples illustrate the invention further.

EXAMPLE 1

Figure 2:
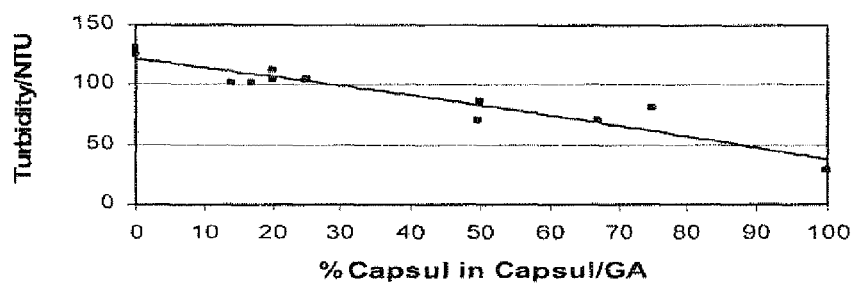
FIG. 2 shows the dependency of the turbidity measured in NTU.
Figure 3:
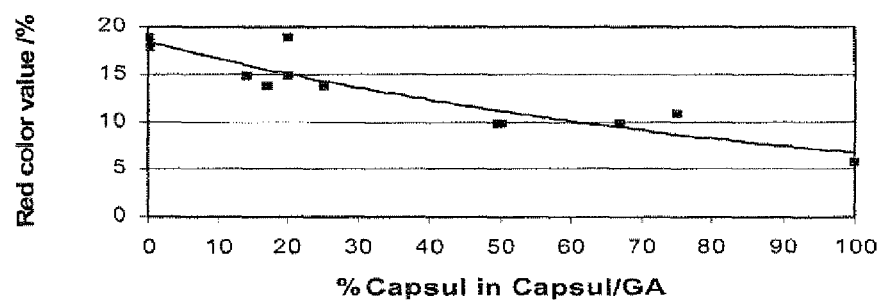
FIG. 3 shows the dependency of the the red value.
Figure 4:
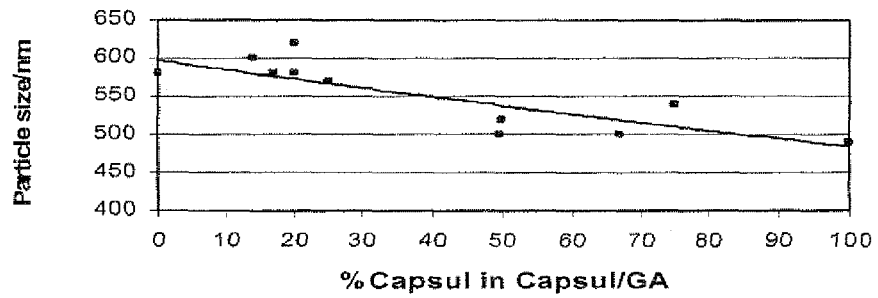
FIG. 4 shows the dependency of the particle size.

Dependency of Physical Properties of Colorant Compositions Containing β-carotene on the Content of Capsul™ (Starch Derivative) Based on the Mixture of Capsul and Arabic Gum FIGS. 1 to 4 show the dependency of the color intensity E 11 corresponding to 494 nm (FIG. 1), of the turbidity measured in NTU (FIG. 2), of the red value (FIG. 3) and of the particle size (FIG. 4) on the content of Capsul (Starch derivatives) based on the mixture of Capsul and Arabic gum in a composition containing about 3 wt-% of β-carotene.

Typically, a powder composition for the use according to the invention comprises a color intensity E 11 corresponding to 494 nm in the range of 1300 to 1900, preferably in the range of 1350 to 1600 and a turbidity measured in NTU in the range of 70 to 250 NTU, preferably in the range of 70 to 120 NTU.

In a preferred embodiment of the invention the powder composition comprises about 25 wt-% to about 80 wt-%, preferably 60 wt-% to 80 wt-% of Capsul™ based on the mixture of Capsul and Arabic gum.

EXAMPLE 2

Preparation of a Colorant Composition a) Preparation of Solution A:

To 530 g of deionized water in a 1.5 l reaction vessel a dry premix of 80.8 g Arabic Gum and 244.7 modified starch (Capsul™) was added at 80° C. The mixture was stirred under inert atmosphere at 72° C. and the pH of the aqueous solution was kept at about 3.9. After complete dissolution of the solids 7.2 g Na-ascorbate, 43.4 g sucrose and 175.o g Maltodextrin DE-2023 were added to the mixture.

b) Preparation of Solution B:

144.6 g of a middle chain triglyceride (Bergabest MCT-Oil 60/40 of Berg+Schmidt) and 0.72 g of dl-α-tocopherol were introduced into a reaction flask. Under inert atmosphere, 25.3 g of crystalline β-carotene and a magnetic stirrer bar was added. The suspension was gently stirred and, at the same time, heated to 170° C. After keeping the mixture at this temperature for about 60 seconds the mixture was re-cooled to about 85° C.

c) Preparation of Emulsion:

While vigorously stirring, solution B was added to solution A at 72° C. and the emulsion was vigorously stirred for about 15 to 20 minutes. A fine emulsion was obtained by a three passage high pressure homogenizing treatment of the preemulsion at a pressure of 50/300 bar (APV-La 1000 Homogenizer).

d) Spray Drying:

To the emulsion 0.2 wt-% of silicic acid (Aerosil 200) was added and at about 65° C. the emulsion was then spray dried in a laboratory spray drier for about 1 hr at an inlet temperature of about 200° C. and an outlet temperature of about 80° C. The spray-dried powder was dried in a vacuum oven at room temperature over night.

e) Analysis:

The mean particle size of the pre-emulsion was about 500-600 nm as measured by photon correlation spectroscopy (Coulter N4 Plus) and the β-carotene content of the powder was 2.9% as determined by spectrophotometry and HPLC-analysis, respectively. The color values L*=87.6, a*=−8 and b*=54 were measured according the CIE-system for a 5 ppm dispersion. Based upon the values of a* and b* a color hue angle h*=82° at a saturation c*=55 can be calculated.
*) GENU Pectin Type VIS of Copenhagen Pectin A/S The composition according to the preparation described above is characterized as follows:

| Substance | Content wt-% |
|---|---|
| Sodium Ascorbate, cryst. | 1.0 |
| Sucrose | 6.0 |
| Maltodextrin DE-2023** | 24.2 |
| Capsul** | 33.8 |
| Gum Arabic** (GA) | 11.2 |
| MCT middle chain triglyceride | 20.0 |
| dl-α-Tocopherol | 0.10 |
| β-Carotene | 3.5 |
| Aerosil 200 | 0.20 |
| % Capsul in matrix | 48.8 |
| % Capsul in GA + Capsul | 75.1 |
| Analytical Data | |
| UV/% | 2.9 |
| HPLC/% | 2.9 |
| E11-corr./494 nm | 1642 |
| E11-corr./463 nm | 1732 |
| L*/a*/b* - 5 ppm | 87/8/54 |
| L*/c*/h* - 5 ppm | 87/55/82 |
| Turbidity/NTU - 5 ppm | 117 |

**Matrix

EXAMPLE 3

Two Further Compositions (2, 3) Prepared According to the Above Mentioned Procedure in Comparison with a Composition (Control) Falling Outside the Scope of the Invention

| Substances | Control Content wt-% | 2) Content wt-% | 3) Content wt-% |
|---|---|---|---|
| Sodium Ascorbate, cryst. | 1.0 | 1.0 | 1.0 |
| Sucrose | 7.0 | 7.0 | 6.0 |
| Maltodextrin DE-2023** | 39.9 | 28.9 | 28.9 |
| Capsul** | 0.0 | 11.0 | 30.0 |
| Gum arabicum** (GA) | 33.0 | 33.0 | 15.0 |
| MCT | 15.3 | 15.3 | 15.3 |
| dl-α-Tocopherol | 0.1 | 0.1 | 0.1 |
| β-Carotene, cryst. | 3.5 | 3.5 | 3.5 |
| Aerosil 200 | 0.2 | 0.2 | 0.2 |
| % Capsul in Matrix | 0.0 | 15.1 | 40.6 |
| % Capsul in GA + Capsul | 0.0 | 25.0 | 66.7 |
| Analytical Data | | | |
| UV/% | 3.5 | 3.2 | 3.2 |
| HPLC/% | 35 | 3.1 | 3.3 |
| E11-corr./494 nm | 1282 | 1392 | 1518 |
| E11-corr./463 nm | 1196 | 1435 | 1714 |
| L*/a*/b* - 5 ppm | 88/10/44 | 88/9/55 | 88/7/66 |
| L*/c*/h* - 5 ppm | 88/45/77 | 88/56/81 | 88/66/84 |
| Red color value % | 18 | 14 | 10 |
| Turbidity/NTU - 5 ppm | 125 | 104 | 71 |

**Matrix

The invention claimed is:

1. A colorant composition comprising a carotenoid dispersed in a modified starch-containing matrix, wherein the composition comprises:
    (a) 10 to about 60 wt. % based on total composition weight of a sugar polymer;
    (b) 5 to 50 wt. % based on total composition weight of gum Arabic;
    (c) 2 to 10 wt. % based on total composition weight of beta-carotene;
    (d) 5 to 10 wt. % based on total composition weight of a mono- or disaccharide;
    (e) 10 to 20 wt. % based on total composition weight of a middle chain triglyceride;
    (f) 0.1 to 2 wt. % based on total composition weight of a water-soluble anti-oxidant;
    (g) 0.1 to 1 wt. % based on total composition weight of silicic acid; and
    (h) 1 to 5 wt. % based on total composition weight water; wherein
    the modified starch of the matrix comprises octenylbutanedioate amylodextrin which is present in an amount of 25 to 80 wt. %, based on the weight of a mixture of the octenylbutanedioate and the gum Arabic, sufficient to impart to the colorant composition a color intensity E11 corresponding to 494 nm of 1300 to 1900 and a turbidity of 70 to 250 NTU.

2. The composition as in claim 1, wherein the fat soluble antioxidant is a tocopherol, a fatty acid ester or a mixture thereof.

3. The composition as in claim 2, wherein the water soluble antioxidant is ascorbic acid.

4. The composition as in claim 1, in the form of a powder.

5. The composition as in claim 1, wherein
    the sugar polymer is Maltodextrin and is present in an amount of 20 to about 30 wt. % based on total composition weight;
    the gum Arabic is present in an amount of 10 to about 40 wt. % based on total composition weight; and
    the beta-carotene is present in an amount of 1.5 to about 10 wt. % based on total composition weight.

6. Food, beverages, animal feeds, cosmetics or drugs comprising a composition as in any one of claims 1 and 2-5.

* * * * *